(12) United States Patent
Larsen (10) Patent No.: US 7,820,433 B2
(45) Date of Patent: Oct. 26, 2010

(54) CULTURE DISH FOR CULTURING BIOLOGICAL CELLS

(75) Inventor: Jacob Møllenbach Larsen, København (DK)

(73) Assignee: Biovir v/Jacob Møllenbach, København NV (DK)

( * ) Notice: Subject to any disclaimer, the term of this patent is extended or adjusted under 35 U.S.C. 154(b) by 937 days.

(21) Appl. No.: 11/630,634

(22) PCT Filed: Jun. 21, 2005

(86) PCT No.: PCT/DK2005/000414

§ 371 (c)(1),
(2), (4) Date: Feb. 2, 2007

(87) PCT Pub. No.: WO2006/000220

PCT Pub. Date: Jan. 5, 2006

(65) Prior Publication Data

US 2008/0090287 A1    Apr. 17, 2008

(30) Foreign Application Priority Data

Jun. 24, 2004    (EP) ................................. 04014805

(51) Int. Cl.
C12M 1/22    (2006.01)
C12M 3/00    (2006.01)
(52) U.S. Cl. ............... 435/305.3; 435/287.5; 435/305.4
(58) Field of Classification Search ............. 435/286.5, 435/287.5, 288.4, 305.1–305.4
See application file for complete search history.

(56) References Cited

U.S. PATENT DOCUMENTS

| | | | |
|---|---|---|---|
| 4,012,288 A * | 3/1977 | Lyman et al. ............ 435/305.2 |
| 4,786,601 A | 11/1988 | Rothenberg |
| 5,449,620 A | 9/1995 | Khillan |
| 5,627,066 A | 5/1997 | Gordon |
| 5,691,194 A * | 11/1997 | Gordon .................... 435/287.1 |
| 5,863,792 A * | 1/1999 | Tyndorf et al. ........... 435/297.5 |
| 5,876,675 A | 3/1999 | Kennedy |
| 6,156,566 A * | 12/2000 | Bryant ..................... 435/305.3 |
| 6,251,343 B1 * | 6/2001 | Dubrow et al. .............. 422/102 |
| 6,448,069 B1 | 9/2002 | Cecchi et al. |
| 6,602,704 B1 * | 8/2003 | Maxwell et al. .......... 435/305.4 |
| 2002/0187078 A1 | 12/2002 | Al-Obeidi et al. |

FOREIGN PATENT DOCUMENTS

FI    884551    *    5/1990
WO    WO 01/88087    11/2001

OTHER PUBLICATIONS

English language abstract for FI884551 which was published May 1990.*

* cited by examiner

*Primary Examiner*—Walter D Griffin
*Assistant Examiner*—Shanta G Doe
(74) *Attorney, Agent, or Firm*—James Creighton Wray; Meera P. Narasimhan (57) ABSTRACT

A culture dish (1) comprising a basic structure (2) with a number of macro wells (4) for culturing oocytes and embryos, the culture dish further comprising a lid (3) with a movable part (8), the movable part (8) having an opening (11) adapted to the size of the macro wells (4), the movable part (8) being movable between a first position where all macro wells are closed by the lid (3) and further positions where for each further position (11) the opening (11) is aligned with one of the macro wells (4) to allow access to this macro well (4) through the opening (11) in the lid (3).

16 Claims, 11 Drawing Sheets

CULTURE DISH FOR CULTURING BIOLOGICAL CELLS

This application claims the benefit of European Application No. 04014805.8 filed Jun. 24, 2004 and PCT/DK2005/000414 filed Jun. 21, 2005, which are hereby incorporated by reference in their entirety.

FIELD OF THE INVENTION

The present invention relates to a culture dish for culturing biological cells, preferably embryonic cells.

BACKGROUND OF THE INVENTION

During the course of in vitro fertilisation (IVF), gamets and embryos are being handled frequently. The handling implies physical handling, for example moving the cells from one culture dish to another, denudation and Intracytoplasmic Sperm Injection (ICSI) and changes in medium composition and physical parameters such as temperature, pH and osmolarity. Normally, gamets and embryos are kept in 4-well culture dishes or 60 mm Petri dishes or the likes. These systems are regarded as open culture systems and as such, $CO_2$ is very difficult to control, because as soon as the lid is removed from the culture dish, $CO_2$ evaporates leading to a change in pH.

Another very important parameter when culturing is temperature. The temperature is very difficult to control within the medium and during handling of embryos (e.g. changing media, microscopy, denudation). It is not unusually to see temperature fluctuations of more than ±2° C., which can reduce the viability of the cells. Using standard Petri dishes in procedures such as in vitro maturation of eggs, in vitro fertilization, 3-day culturing of embryos, culturing to the blastocysts stage, etc. require handling of the individual cells/embryos several times for each procedure. How much this reduces the potential of the cells is difficult to say, but each time the embryo is being handled, it involves a risk of physical damage, a change in temperature and pH and contamination from the surroundings, which all are factors reducing the viability of the cell or the implantation potential of the embryo. Thus, there is a need for designing a culture dish that can optimize culture conditions during IVF.

Additionally, practical handling of the conventional dishes is not optimum. In order to lift a dish, one must lift both the bottom of the dish and the lid at the same time. If the operator is not careful, the operator will only lift the lid with the result that the dish is dropped.

Despite the increase of the industry related to IVF, advantage is primarily taken of general experience in in-vitro cell culturing and only relatively few attempts have been made to develop apparatus especially designed and optimised for IVF.

US patent application no. 2002/0187078 A1 describes a multi-well plate for holding a chemical compound for heating in a microwave oven. The plate is a planer member having arrays of rows and columns in its surface. The plate has heat reservoirs in the form of fluid filled channels positioned lengthwise along the side portions of the plate.

U.S. Pat. No. 4,786,601 describes a tissue culture holder which has an insulating chamber in its base below the culture wells. The insulating chamber is filled with air or a clear liquid, and it may be sealed or may have passageways for circulating air through the chamber and up into the space above the wells.

U.S. Pat. No. 5,876,675 describes a microfluidic device. One embodiment of the invention relates to a microfluidic device, which incorporates a manual handling structure. This manual handling structure is shown as inwardly tapered or insert edges, at opposing edges of the device.

Especially designed for IVF are aspects in the following disclosures with compartments to culture embryonic cells.

U.S. Pat. No. 5,484,731 describes a multi-well In Vitro Fertilization (IVF) plate. The plate is equipped with a removable lid divided into adequate sections. Each section may be moved by a sliding movement from a closed position into an open position, thereby each exposing a plurality of wells.

U.S. Pat. No. 6,448,069 describes an embryo culturing method and apparatus including a culturing container such as a Petri dish. The culturing container contains a number of compartments made from a plurality of spaced-apart pickets which combine to form four compartments. The pickets serve to form liquid permeable barriers between adjacent compartments, and also between the growth enhancing nutrient.

U.S. Pat. No. 5,449,620 describes a method and apparatus for culturing embryonic system cells. The apparatus provided in this invention comprises a solid support such as a Petri dish having a plurality of tapered depressions in the bottom wherein a controlled concentration of a selected cell-type may be layered into each depression. The depressions have a diameter of about 0.2-0.3 mm at the top and 0.1-0.2 mm at the bottom.

U.S. Pat. No. 5,627,066 describes a method and apparatus for In Vitro Fertilization. The apparatus provided in this invention comprises a culture dish which is equipped with a number of micro-chambers. Each micro-chamber has a volume which exceeds the volume of an oocyte to be fertilized. The volume of the chamber is generally 8 to 20 times the volume of an oocyte.

International patent application WO 01/88087 describes an apparatus for micro-fluidic handling of embryonic cells including a transport network formed by a generally embryo scaled channel (micro-channels) is disclosed.

Finnish patent application FI 884 551 by Jukka Häyrinen discloses a culture dish comprising a basic structure with a number of macro wells for culturing oocytes and a rotatable lid with openings adapted to a row of macro wells such that when the opening is aligned with this row of macro wells, access is possible to four macro wells through the opening in the lid. The access to at least four wells at a time leads to unnecessary evaporation of carbon dioxide unnecessary heat loss, which is a disadvantage.

U.S. Pat. No. 5,891,712 discloses a drop culture dish with indentations in the bottom with alphabetical markings.

Micro channels for oocytes are disclosed in S. M. Willadsen "A method for culture of micromanipulated sheep embryos and its use to produce monozygotic twins". Nature Vol. 277, pp. 298-299, Jan. 25, 1979 and in H. H. van der Ven et al. "Fertilization of human oocytes in capillary tubes with very small numbers of spermatozoa", Human Reproduction Vol. 4 no. 1 pp. 72-76, 1989. Micro-channels with barriers to hold an oocyte in, while it is exposed to fluid flow through the channel is disclosed in U.S. Pat. No. 6,193,647 or reported in Glasgow et al. "Individual embryo transport and retention on a chip" published in Micro Total Analysis systems 1998, p. 13-18, October 1989, and in H. C. Zeringe et al. "Micro fluidic single embryo in PDMS", presented at $21^{st}$ Ann. Int'l. Conf. of the IEEE Eng. in Med. and Bio. Soc. and the 1999 Ann. Fall Meeting of the Biomed. Eng. Society, Atlanta, Ga., Oct. 13-16, 1999.

Though, the abovementioned specially designed culturing dishes have improved the handling of oocytes for IVF, still needs for improvements exist. Especially aspects like reduced evaporation of carbon dioxide, pH stability and reduced heat loss are of concern.

DESCRIPTION/SUMMARY OF THE INVENTION

It is therefore the object of the invention to provide a dish for IVF with improved applicability, especially with reduced evaporation of carbon dioxide, implying enhanced pH stability.

This object is achieved by a culture dish comprising a basic structure with a number of macro wells for culturing oocytes, the culture dish further comprising a lid with a movable part, the movable part having an opening adapted to the size of the macro wells, the movable part being movable between a first position, where all macro wells are closed by the lid and further positions where for each further position, the opening is aligned with one of the macro wells to allow access to only one macro well at a time through the opening in the lid.

Thus, according to the invention, the lid does not have to be lifted off in order to access the wells. A lifting of a lid causes substantial convection of the air around the lid and increases the evaporation, whereas a gentle rotation or sliding action reduces convection. Furthermore, due to the construction of the culture dish, only one well is accessible at a time. Even if the access to a well lasts for a substantial amount of time, the other wells are not affected, because no evaporation and temperature change occurs as no lid is opened over all the wells. Overall, unnecessary evaporation of especially $CO_2$ is prevented, which implies enhanced pH stability. Furthermore, heat loss is reduced for the other wells.

In a practical embodiment, the movable part, typically made of a transparent material, is a rotational disc that is rotatable between the first and the further positions. In this embodiment, the macro wells would be arranged in a circular manner. Alternatively, the movable part could be a sliding arrangement. In this embodiment, the macro wells could be arranges linearly. However, other embodiments are possible.

In comparison with the culture dish as disclosed in the above mentioned Finnish patent application FI 884 551, the culture dish according to the invention has another advantage. In the culture dishc of FI 884 551, the entire lid is rotated in order to open or close the wells. in addition, the lid extends around the edge of the underlying dish. This implies that the rotation cannot be performed with one hand—or at least can only be performed very hardly been performed with one hand. However, for the medical assistant, a one hand opening and closing is highly desirable. For a culture dish according to the invention, the lid itself is not to be rotated in order to get access to a single well, but only a part of the lid has to be moved. Thus, the culture dish with the lid can be held in one hand, where, for example, the thumb of the same hand is easily used for moving/rotating the movable part, such as a rotatable disc on the lid.

As will be apparent from the following aspects, the culture dish according to the invention provides a number of related solutions in order to improve the art of culture dishes for IVF, though the dish can be used for other purposes as well. Further means for reducing heat loss during handling of the culture dish is giving in the following embodiment.

The basic structure may comprise a bottom cup and a covering top part containing the wells. A cavity between the top part and the bottom cup may be filled with a liquid, typically water, in order to act as a heat reservoir into which the walls of the wells extend for thermal contact with a fluid in the cavity. In order to be optimal efficient, the cavity may extend not only around the side walls of the wells but also underneath the bottom of the wells. As the volume of the cavity is larger than the volume of the wells, liquid in the cavity functions as an efficient temperature buffer for the culture medium in the wells. When the culture dish is removed from a temperature stabilised environment, heat loss is reduced substantially in comparison with culture dishes without liquid reservoir in thermal contact with the wells. This is especially important, if the handling takes place on benches with laminar air flow, where the air has a lower temperature.

Also, when the culture dish is placed on a heating plate, for example in an incubator, the heat transfer from the heating plate to the culture medium in the wells is gentler, because it has to traverse the liquid in the cavity first.

In order to assure a proper heat transport from a heating plate to the temperature buffer liquid, the outer side of the bottom part is plane. Typically the bottom cup or the top part or both are made of a transparent material, for example polymer. This way, cells in the dish are easily observed through a microscope without opening the lid.

The macro wells may be provided with a number of depressions or micro wells for keeping the oocytes or embryos protected from floating around during fluid convection in the macro well. By placing one oocyte or embryo in such a micro well, the operator knows the location of it and does not have to search for it in the medium. A possible form of the micro wells is cylindrical, for example with a diameter of 0.4 mm or larger, even with diameters of 44 mm, and a depth of 0.3-0.7 mm optionally implying a conical top for easier access and pipetting. In addition, the macro wells may contain a slightly larger micro well for semen. The slightly larger micro well may be connected to the oocyte micro wells with channels for leading spermatozoa from the semen micro well to the oocyte micro well.

The culture dish may also comprise at least one pair of handling wells, typically a number of pairs of handling wells, where the two handling wells of the at least one pair are connected by a micro channel. The diameter of such a micro channel may have a size adapted to the size of an oocyte, for example with a diameter that is only slightly larger than an oocyte or with a diameter that is up to a few times the diameter of an oocyte. Such micro channels may be used for fertilisation in the channel or for the first/initial culture periods of embryos. The advantage is that the micro channel is so narrow that fluid that flows through the channel are forced into the very near vicinity of the oocyte, for example for flushing and cleaning the oocyte. By reducing the volume of media, it is easier to control the amount of carbon dioxide, $CO_2$, and the oxygen, $O_2$, in the medium, because the diffusion constant is reduced. Additionally, by reducing the volume, the autocrine/paracrine substances released by the cell will not be diluted as seen in culture systems with much larger volumes, which is regarded as an advantage with regard to the fertile/implantation properties or potential of the oocyte/embryo.

In order to prevent the oocyte to be flushed out of the micro channel accidentally, the micro channel may comprise a resting chamber with an obstacle that prevents the oocyte to pass the obstacle but which allows fluid to pass it. The obstacle may, for example, be a grid with an adapted mesh size.

The at least one pair of handling wells and the micro channel may be constructed as a unit that may be placed into the top part and exchanged from the top part if desired. For example, such units may be prepared and placed in a different location for storage with medium and placed into the top part when needed.

The culture dish may comprise a temperature indicator for indicating the temperature of culture medium in the wells. For example, the temperature indicator may imply built-in micro sensors or a temperature strip with temperature indication by changing colours or changing intensities. As the temperature of the culture in the wells is approximately equal to the temperature of the liquid in the cavity, the sensor may be placed in thermal contact only with the cavity liquid. The advantage is that there is not direct contact of the temperature sensor with the culture medium of the oocytes, such that any concern about contamination of the oocytes due to possible non sterility of the temperature sensor is prevented.

The culture dish could also contain an electronic identification of the culture dish as seen in the RFID (Radio Frequency Identification) technology. It is very important that the individual culture dish can be identified such that no mistake it being committed when transferring the cells back into the patient. Also this technology could be coupled with a similar tag or id bracelet that the patient is carrying. This way, the dish (with the cells) and the patient may be coupled. In a computer database identification of dishes may be stored and related to specific patients. Therefore, the invention also implies a combination of such a culture dish with an ID indicator intended to be worn by a person to which the culture dish is related, wherein the ID indicator and the RFID tag have means for mutual association, for example identical ID numbers.

In addition to a unique identification, production data could also be added, for example production date, batch number etc.

RFID technology could also be used to generate data in the lab that shows the time when the dish is removed from the incubator, how long the culture dish was outside the incubator who performed this operation etc. Each time a person handles the dish, the tag inside the culture dish is read by a RFID reading device. This could be a valuable tool in the quality control of the clinic and important documentation against lawsuits from e.g. patients.

The culture dish according to the invention may comprise passive RFID tags which do only response to calling RF signals by a transmission of the identity of the tag. By incorporating these tags into the dish, the information can be read in an identification and control zone, ID zone, which is a radio transmitter/receiver with connected computer system that can be build into the IVF workstation, where cells are handed manually. All data storage is then performed by a computer system connected to the RFID reading device. For example, the system may store the time, when culture dishes are removed from the incubator and when they are replaced. In addition, handling at different work stations may be recognized by the ID zone and stored for later control.

Alternatively, the culture dish may comprise an active system with a microprocessor and an RFID tag. In the latter case, parameters such as but not resticted to temperature, carbon dioxide concentration and/or pH, or other metabolic parameters measured by suitable sensors that are connected to the micro processor, may be transferred as digital data to the micro processor and stored therein, after which the data can be read from the micro processor by using RFID technology.

By incorporating these RFID tags into the culture dish, temperature logs could be generated enabling the embryologist in retrieving this very important information. This data are valuable for validating and controlling the culture period. Temperature or stable temperature conditions are believed to be of highest importance in cell culturing. For example, the micro processor or the computer system may initiate an alarm in case that the culture dish is removed from the incubator for a time length above a predetermined value, or if the parameters such as temperature, carbon dioxide content, pH or others deviate from a pre-set intervals.

The temperature could be read in the water reservoir around the dishes such that the sensor does not come into contact with the culture itself in the well. This minimizes the risk for contamination. A carbon dioxide sensor may measure the carbon dioxide content in the gas above the culture and would also be prevented from contaminating the culture.

An active heat element could be build into the dish as well, so the dish itself would be a self contained unit.

In order to minimize the risk for mistakes, the culture dish according to the invention may comprise indicators for different time settings. For example, the culture dish may have a part of it coloured in a special colour, where the colour indicates the day of the week, where the cell sample has been cultured. This part could among others be the lid without the rotating disc being coloured. Colouring only the lid has the advantage that microscopy of the cell culture would not be influenced, because the bottom of the well would still be clear, and the rotating disc would be clear as well. It is envisaged that such a colour indication could be obtained by a clearly recognizable but only slight colouring of the clear plastic lid.

The lid of the culture dish is supported by the top part or the rim of the bottom cup or by a combination of these. The structure of the basic part is made such that in one position, the lid rests tightly over the wells and substantially closes the wells, whereas in a second position, for example in a 90 degrees or 180 degrees rotated position, the lid rests with a slight distance over the wells. This semi-closed position is desirable when the culture dish is placed in a $CO_2$ incubator with $CO_2$ exchange between the gas in the incubator and the culture medium in the well.

When a culture dish is outside the incubator, condense may appear on the lower side of the lid. To prevent that condensation on the lid is scraped off and runs down into one of the wells when turning the lid, the lid is elevated when turned thereby preventing condense to be scraped off. On the other hand, the lid may be desired to be tightly above the wells when no wells are accessible. For this reason, in a further embodiment, the lid is lowered when in a position where all wells are closed and lifted slightly when turned towards the position where one well is accessible. Such a lifting movement can be achieved by an upward sliding mechanism on a ramp during rotation. If using smooth material as polymer, the rotation of the lid can be performed by the gentle moving touch of a single finger, even when a lifting-lowering mechanism on a ramp is applied. Alternatively, the movable part, such as the disc, may be scooped out on those locations that normally are located above the macro wells. In this case, condensations will be located in these hollows and will not be scraped off during movement of the movable part.

As it is apparent from the foregoing, the culture dish according to the invention has a number of related features for improvements over known techniques. Using macro wells, handling wells and micro-channels, a culture dish according to the invention may be used for the complete culturing of oocytes including the fertilisation process. The combination of macrowells and microchannels gives and all-in-one culture system optimizing fertilization and culture (by reducing culture volume, and thereby creating a microenvironment) and eases handling by reducing handling of the cells. Using only one dish eases the work of the operator and reduces the risk for mistakes and accidents.

SHORT DESCRIPTION OF THE DRAWINGS

The invention will be explained and examplified in more detail with reference to the drawings, where.

DETAILED DESCRIPTION/PREFERRED EMBODIMENT

Figure 1:
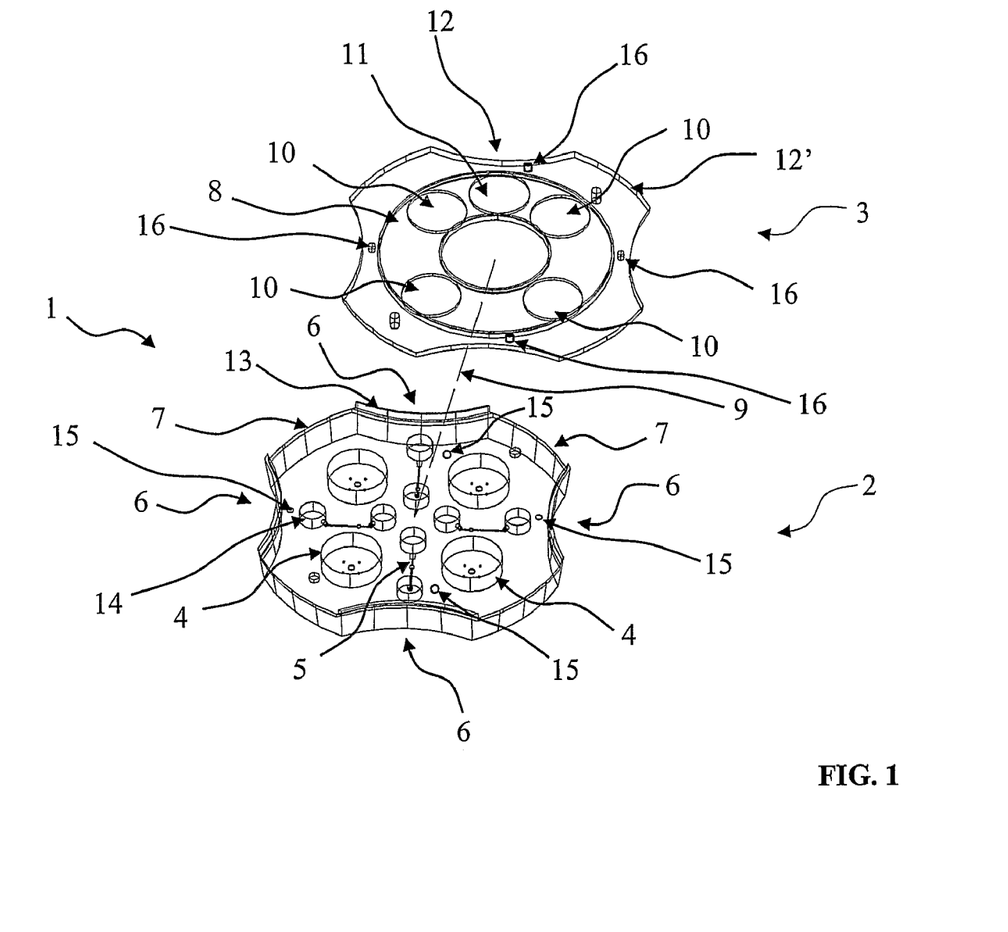
FIG. 1 shows a drawing of the culture dish.

In FIG. 1, an embodiment of the culture dish 1 according to the invention is illustrated. The culture dish 1 comprises a basic structure 2 and a lid 3. The basic structure 2 comprises a plurality of macro-wells 4 for culturing oocytes and embryos and handling wells 14 pairwise connected by micro-channels 5 for fertilisation.

Figure 3:
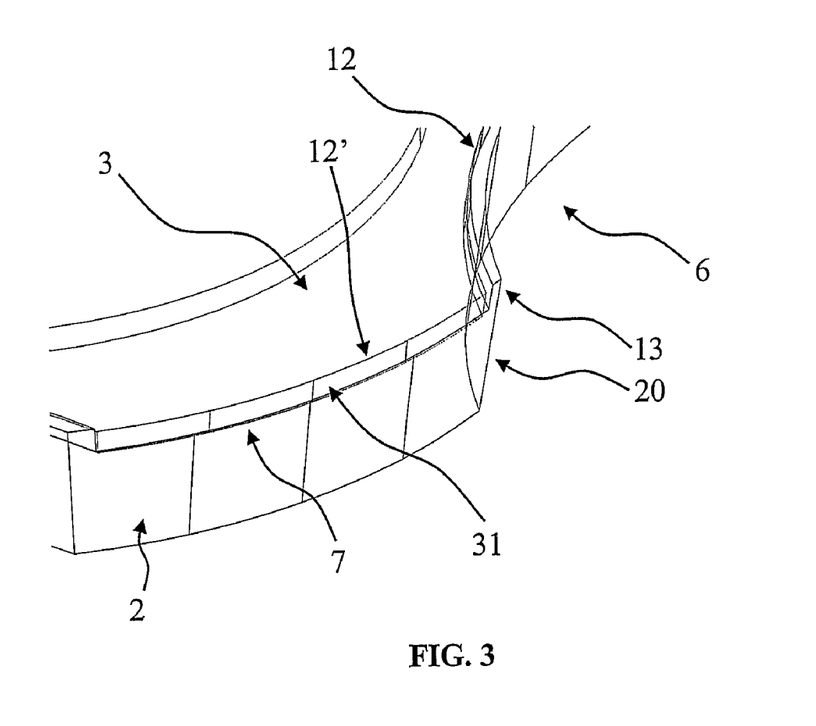
FIG. 3 shows how the security lid and the handling grips are integrated parts of the overall design of the culture dish.

The culture dish 1 is equipped with four handling grips 6 which have upstanding lips 13, shown in more detail FIG. 3, between which the lid 3 during use rests in recesses 7. The upstanding lips 13 embrace the lid 3 at concave part 12 of the rim such that the lid 3 is not accidentally lifted off the dish 1 when handled by the handling grips 6. Thus, the handling grips 6 make it safer to carry the culture dish 1. On the other hand, when the lid 3 is to be lifted off the dish 1, this is easily performed by a gripping action with fingers placed on convex part 12' of the rim of the lid 3 on opposite recesses 7, in which the lid 3 is supported and extends outside the periphery of the basic structure 2. This is seen in more detail in FIG. 3.

There are shown 4 handling grips 6, but it should be apparent to anyone skilled in the art that the number of handling grips may be different than depicted in FIG. 1.

The lid 3 is equipped with a rotational disc 8 whish can be rotated around the axis 9 as depicted by a dashed line. The lid 3 underneath the rotational disc 8 is equipped with four windows 10 corresponding to the macro wells 4, and the rotational disc 8 comprises an opening 11 which by rotation can be aligned with one of the windows 10 in order to give access to the macro wells 4 below the aligned window 10. With the rotational disc 8 in the lid 3, it is only possible to expose one macro-well 4 at a time. Thus, this functionality substantially reduces the evaporation of $CO_2$ from the macro-wells 4 and hence enhances the pH stability as well as the temperature stability inside the macro-wells 4. This functionality is of crucial importance for the viability of the cultured cells.

In the shown embodiment, either one macro well 4 will be accessible at a time or one handling well 14 in order for the other wells 4, 14 to be covered. For this reason, one of the handlings wells 14 or one of the macro wells 4 may be a dummy and not for culturing use in order to have a position of the opening 11 in the lid 3, where all wells are covered.

Also indicated in FIG. 1 are downwards directed, ring-formed elevations 17 that function as scoops in which condensed water can accumulate without being scraped off the disc 8 during rotation of the lid 3. By preventing this accumulated water from being scraped into the macro wells, the risk for contamination is reduced.

Figure 2:
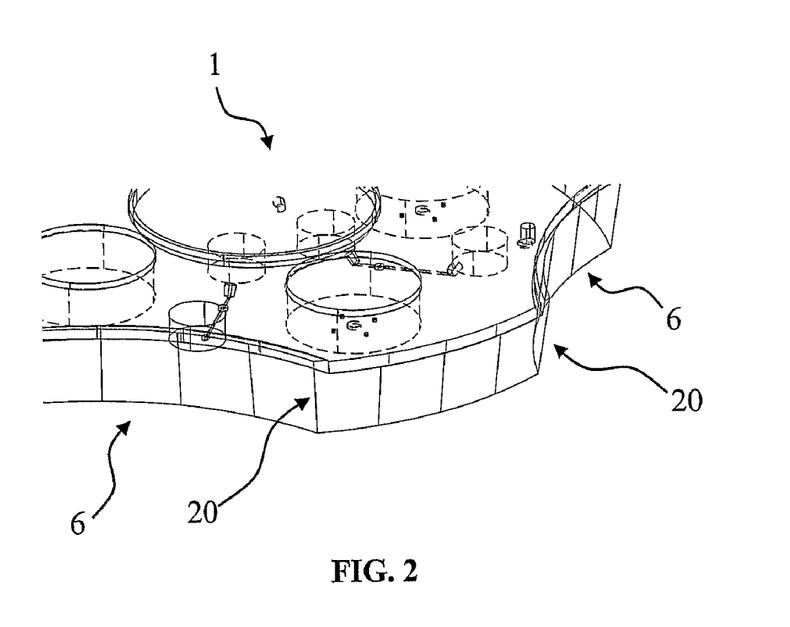
FIG. 2 shows a close-up view of a section of the culture dish.

In FIG. 2 a close-up view of a section of the culture dish 1 is shown, where the ergonomic design of the-culture dish 1 is depicted. The handling grips 6 have inwardly tapered edges with a negative slope 20 toward the bottom of the culture dish 1. The curvature of the grips 6 should be such that the culture dish 1 is convenient to hold in a hand. Grips 6 in the form of arcs with a radius in the order of 36 mm or larger has been proved to be convenient. The ergonomic design gives a better grip when carrying around the culture dish 1, and the inwardly tapered slope 20 of the handling grips 6 reduces the risk of dropping the culture dish 1 when carrying it around.

FIG. 3 gives a view of how the security lid 3 and the handling grips 6 are integrated parts of the overall design of the culture dish 1. The grips 6 are negatively inclined with a slope 20 of minimum 8 degrees. When the security lid 3 is placed on the basic structure 2 in the recesses 7, concave part 12 of the rim of the security lid 3 lies behind the lips 13, thus making it impossible to lift the security lid 3 of by an accident when gripping the concave grips 6. When the security lid 3 needs to come off the lid 3, it is lifted at the edge 31 of the convex part 12' of the rim of the lid 3 in the recesses 7. This poses a tremendous advantage as compared with conventional Petri dishes in which the edge of the lid is outside the edge of the dish itself. The use of conventional Petri dishes may lead to accidents because the person who handles the dish only gets a grip around the lid instead of the dish itself. It is important to avoid such accidents because the supply of for example oocytes and embryos are may be scarce. Moreover, it may be associated with some risk to the implicated individuals if further operational surgery is needed in order to secure a new supply of oocytes, which again is added to the psychological stress of the implicated individuals and their relatives.

The culture dish is provided with four small holes 15 in the basic structure 2 corresponding to four pins 16 which fit into the holes 15 only for a certain position. In this position, the lid 3 fits tightly to the basic structure 2 in order to prevent evaporation from the wells 4, 14. If the lid is placed in a 180 degrees rotated orientation on the basic structure, the pins 16 are offset with respect to the holes 15 such that they do not any longer fit into the holes 15 but rest on the surface of the basic structure 2. In this position, the lid 3 is placed in a semi-closed position where it is possible to ventilate the culture wells.

Figure 4:
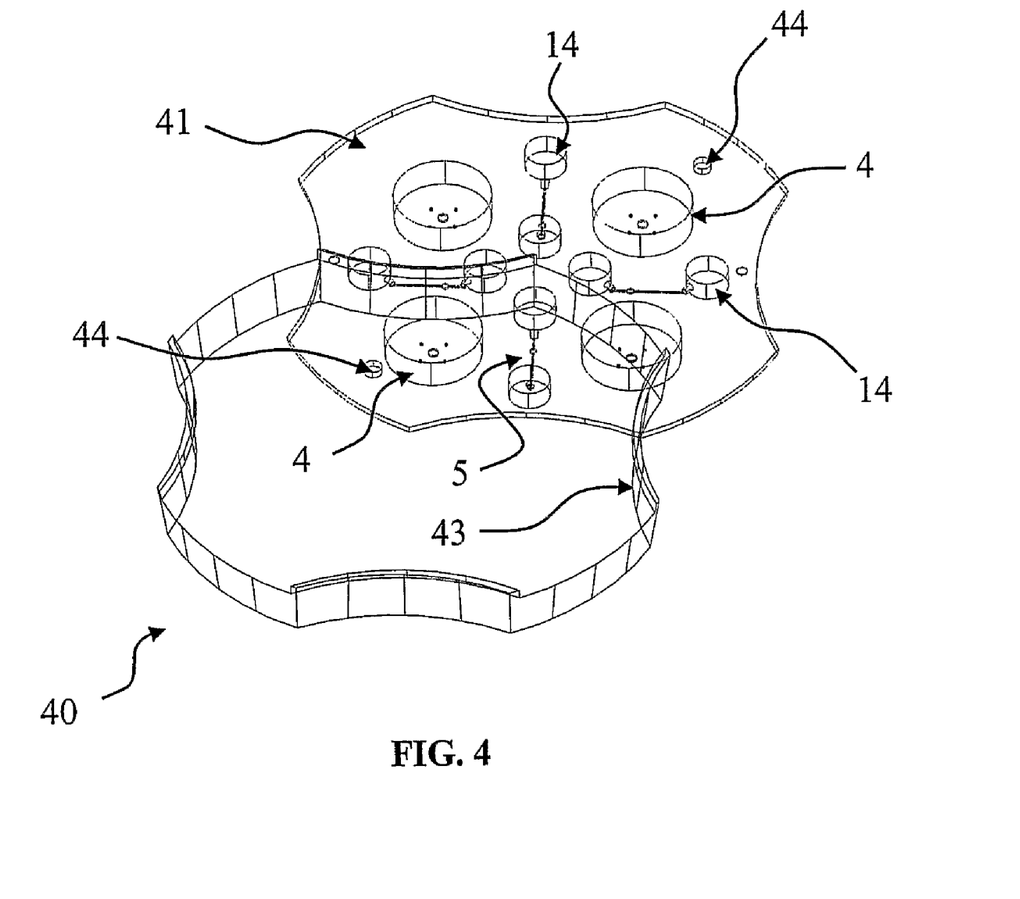
FIG. 4 shows a basic structure which comprises a top part and a bottom cup.

In FIG. 4 is illustrated a basic structure 2 which comprises two main parts: A bottom cup 40 and a covering top part 41. The top part 41 may be equipped with four macro-wells 4 and four micro-channels 5, each connecting a pair of handling wells 14. It is stressed at this point that other configurations of wells and micro-channels 5 may be advantageous under certain circumstances and that the present invention by no means is restricted to this configuration which is merely meant as an illustration.

The top part 41 and the bottom cup 40 may be constructed as one piece or as two mutually demountable parts. In the latter case, the same bottom cup 14 may be reused with different top parts 41. This makes it possible for the manufacturer to produce and sell spare top parts 41 with a plurality of configurations of wells and channels applicable for a wide variety of purposes. Furthermore, it is more cost efficient and environmentally acceptable to the user of the culture dish 1.

The top part 41 is designed such that due to the negative slope 20 of the periphery of the bottom cup 40 toward the bottom, the edge of the top part 41 will rest on the inner sides 43 of the edge of the bottom cup 40, thus, leaving a cavity between the bottom of the bottom cup 40 and the top part 41.

The cavity between bottom cup 40 and the top part 41 may be filled with a transparent sterile liquid. The liquid may be added through two holes 44 in the top part 41. It should be apparent to anyone skilled in the art that the numbers, size, and position on the holes 44 may, according to the invention, be different than depicted in FIG. 4.

This transparent sterile liquid is a part of the Temperature Stabilizing System (TSS) of the culture dish 1. The use of a temperature buffer liquid that completely fills the cavity between the bottom of the bottom cup 40 and the top part 41 and which completely surrounds the culture wells will substantially reduce the temperature variations in the culture medium of the wells 4, 14. A fabrication of the bottom cup 40 and the top part 41 with transparent material implies a minimised interference with observation of the cells in the culture dish 1 if a transparent liquid is applied. In fact, a water layer between the bottom and the middle layer actually improves visibility, just a drop of water between an object glass and cover glass. Heat is transferred to this liquid by means of conduction from a heated surface through the temperature buffer liquid that surrounds the wells, or heat can also be transferred by means of convection as is the case when the culture dish 1 is placed inside an incubator.

The special security lid 3 is also part of the TSS system and important part in reducing temperature variations. The lid 3 insulates and since it only discloses one well 4 at a time the evaporation from the wells 4 are kept at a minimum and there by reduces heat loss.

Figure 5A:
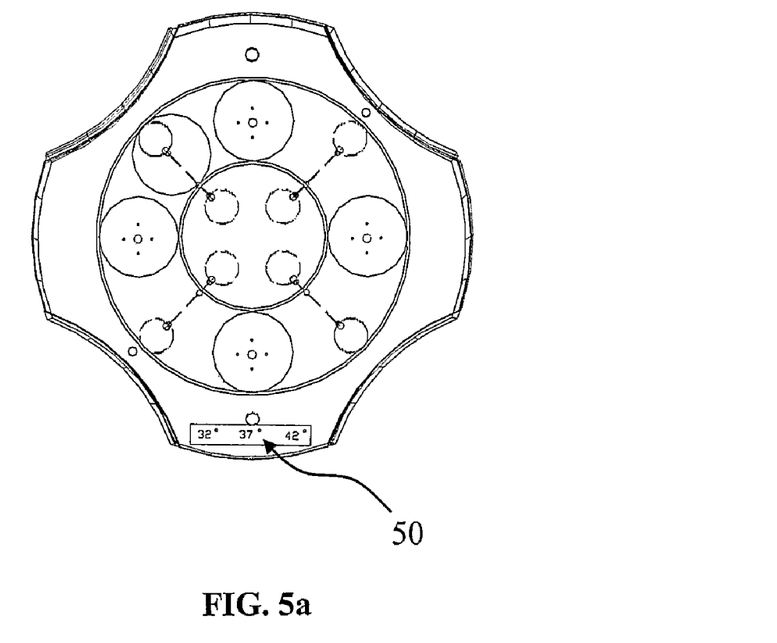
FIG. 5a shows an embodiment of the invention where a temperature sensor is built into the culture dish.
Figure 5B:
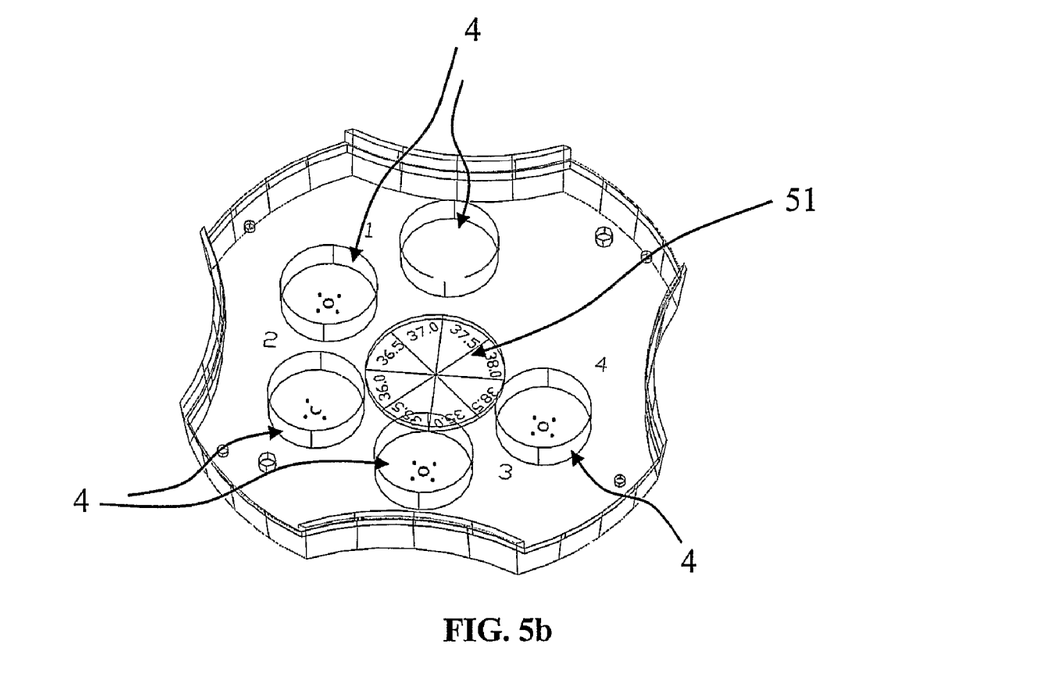
FIG. 5b shows another embodiment of the invention where a temperature sensor is built into the culture dish.

In FIG. 5a is illustrated an embodiment of the invention where a temperature sensor 50 is built into the culture dish 1. The temperature sensor may be incorporated in the reservoir of the TSS system. The temperature of the reservoir and medium is roughly the same or it will deviate by a certain small amount, thus, the sensor gives an indirect measure of the temperature in the medium. In FIG. 5b is illustrated another embodiment of the invention where a temperature sensor 51 is placed in the centre of the culture dish 1.

There are several reasons for placing the sensor in the reservoir: Embryologists will be concerned about contamination of the embryos if placed in the same place as the cells and secondly, the sensor could block the view for doing microscopy. At this point it is stressed that the culture dish 1 may be used to culture other kind of cells than embryonic cells, but since IVF may be the main usage of the culture dish 1, it is repeatedly referred to this science in the present application. The built in temperature sensor 50 and 51 could alternatively be a micro sensor or a LC temperature strip.

Figure 6A:
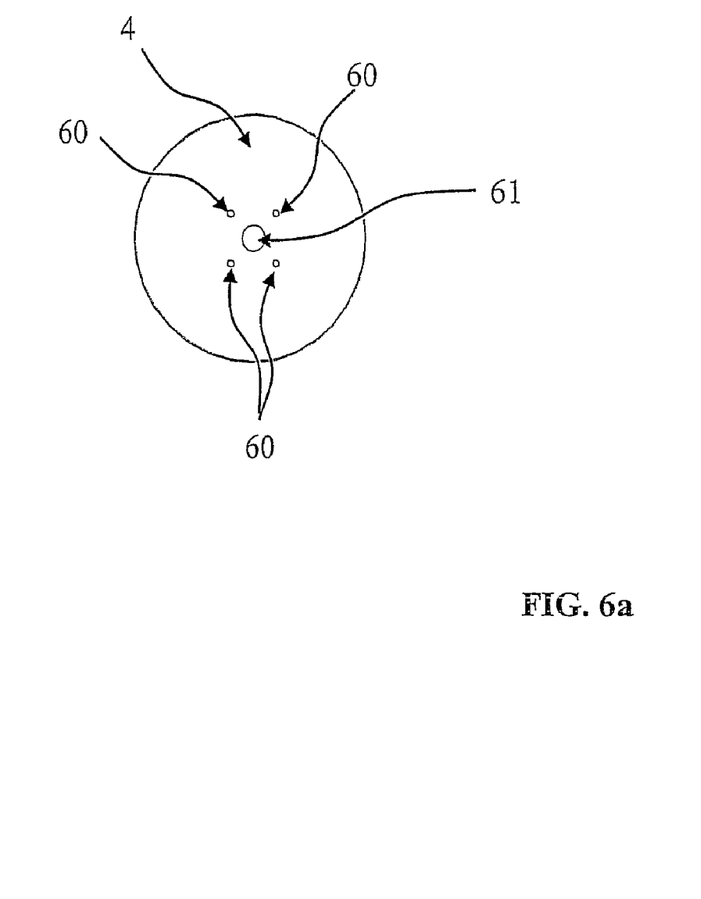
FIG. 6a shows an embodiment of the macro-well.
Figure 6B:
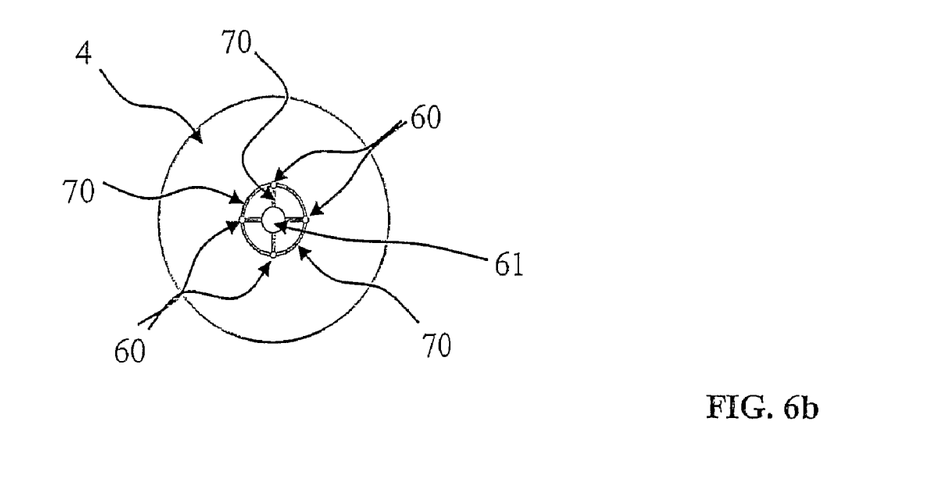
FIG. 6b shows an alternative embodiment of the macro-well.

In FIG. 6a, a macro-well is shown with four micro-wells 60 for the oocytes and one larger micro-well 61 for semen, placed in the middle of the four micro-wells 4. In FIG. 6b is illustrated another embodiment of a macro-well 4 comprising four micro-wells 60 for the oocytes and one micro-well 61 for semen, where the semen micro well in the micro-well 61 is connected by channels 70 to the micro-wells 60 containing the oocytes. The channels 70 guide the sperm cells to the oocytes and optimize fertilization.

Figure 6C:
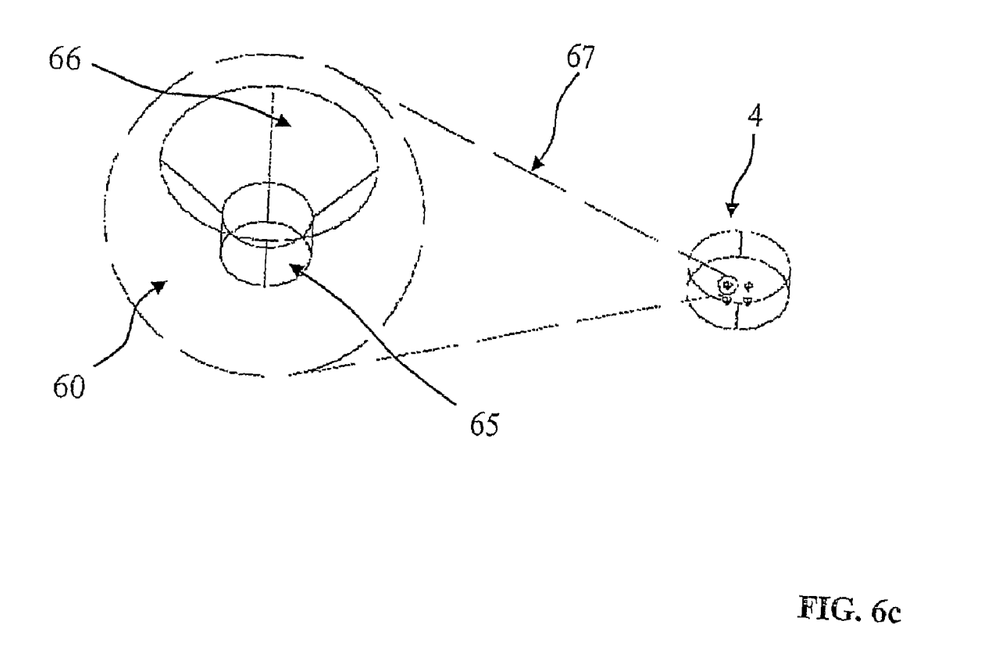
FIG. 6c is a close up illustration of a micro well.

In FIG. 6c, a possible configuration of a micro well 60 is shown as an enlargement indicated by the cone 67. The micro well 60 has a cylindrical lower section 65 for resting of the oocyte/embryo and a tapered upper section 66 for easy pipette access.

Figure 7:
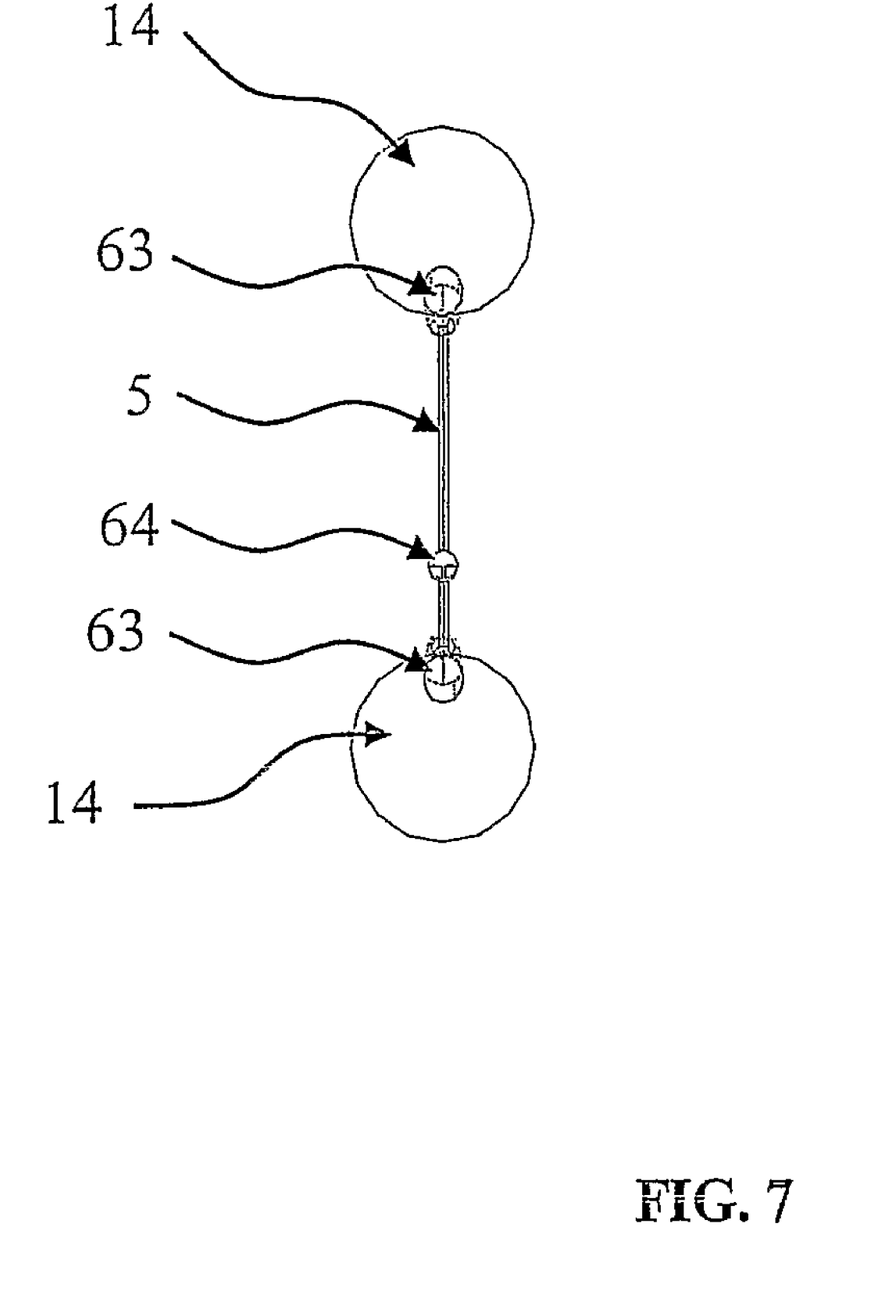
FIG. 7 shows an embodiment of the handling wells and micro-channels.
Figure 8:
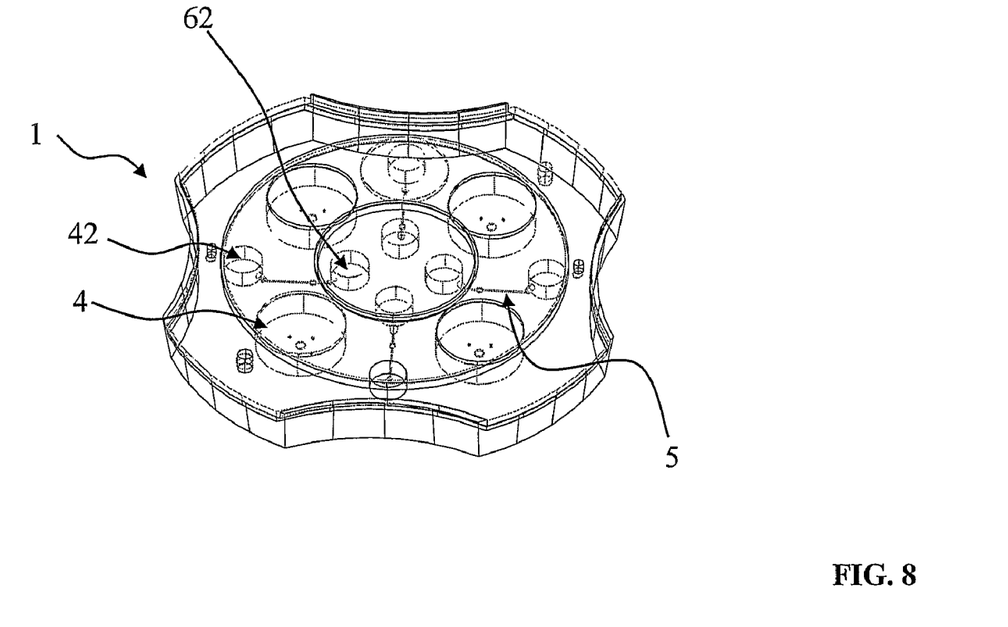
FIG. 8 shows an embodiment of the invention where the relative position of the macro-wells and micro-channels are shown.

In FIG. 7 is illustrated an embodiment of a pair of handling wells 14 with a micro-channel 5, where the over all shape of the micro channel may be mainly cylindrical. In FIG. 8 is illustrated an embodiment of the invention, where the relative position of the macro-wells 4 and micro-channels 5, are shown.

Figure 10:
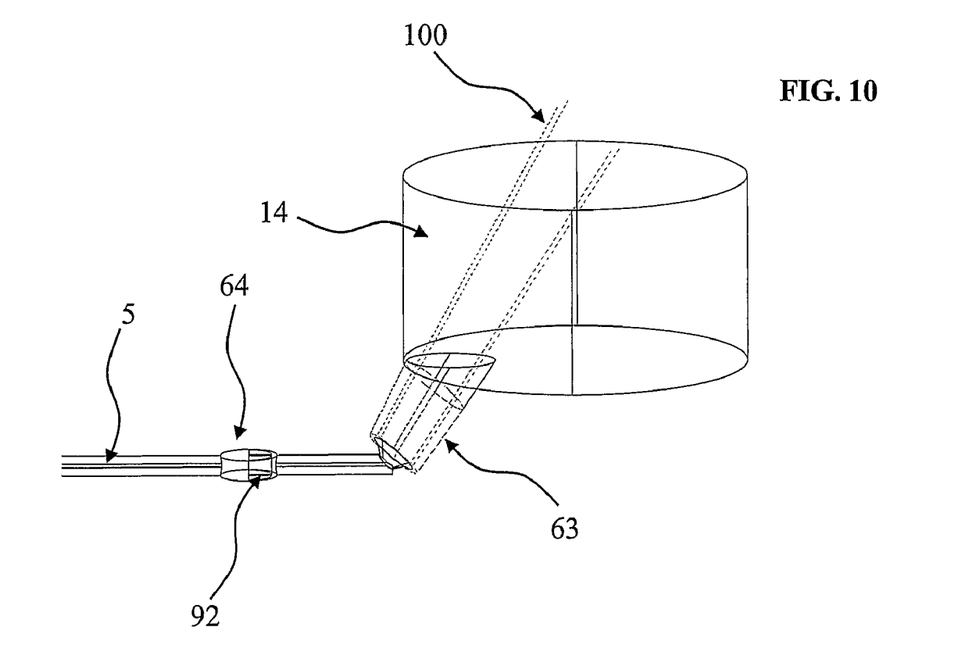
FIG. 10 shows a close-up view of the handling well.

The handling wells 14 make it possible to handle the cells within the micro culture channel 5. This handling can be performed by pipettes as is illustrated in more detail in FIG. 10 which is a close-up view of the handling well 14. This kind of handling wells 14 where ordinary pipettes may be used to introduce medium or cells and to create pressure or vacuum in the micro culture channels 5 is advantageous, since no speciality tools are necessary for handling the cells while inside the micro culture channel 5. The tip 100 of a pipette is shown as dashed lines. The unique functionality of the design shows how the tip 100 of a pipette fits the nozzle construction 63 of the micro culture channel 5. The inclination of this nozzle construction 63 makes it possible to do microscopy at the same time as pipetting. The nozzle construction 63 is placed at either end of the micro channel 5.

Figure 9:
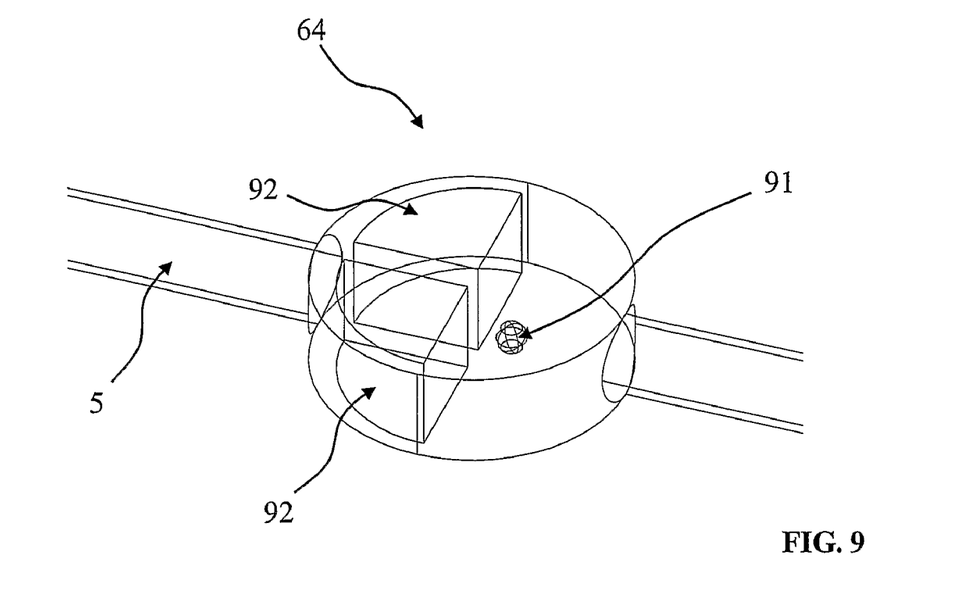
FIG. 9 shows an embodiment of the so called resting chamber.

When inserted into the micro channel, oocytes 91 may be placed in the resting chamber, which is shown in more detail in FIG. 9. In FIG. 9 only one embryo 91 is shown, but there is no hindrance for several embryos may be placed in one micro-culture channel 5 at the same time.

Embryos may be inserted into the micro channel 5 by flushing them into the channel through the pipette 100. In turn, oocytes may be removed from the micro-channel 5 by applying vacuum. Vacuum is created by pipettes or the like. Pressure and vacuum is applied to transport cells, add and remove medium and removal of cumulus cells.

Another property of the micro channel 5 is that it may be inclined in such a way that by the force of gravity, the embryo may be mowed towards the resting chamber 64 of the micro culture channel 5.

In FIG. 9 is illustrated an embodiment of the so called resting chamber 64, comprising an embryo 91. An obstacle 92 is used to prevent the embryo 91 to escape the micro channel 5 when performing denudation, change of medium or the like. The special obstacle 92 makes it possible to remove the cumulus complex from an embryo while inside the resting chamber 64. The obstacle 92 also prevents the embryos 91 from being sucked out during medium change or other handling.

The functionality of the culture dish makes it possible to observe the cells with both stereo microscopes and inverted microscopes. The resting chamber 64 (resting during culture) may also used for observation at the same time. The cells can be monitored without removing the lid 3, as the material of the dish is transparent.

Figure 11:
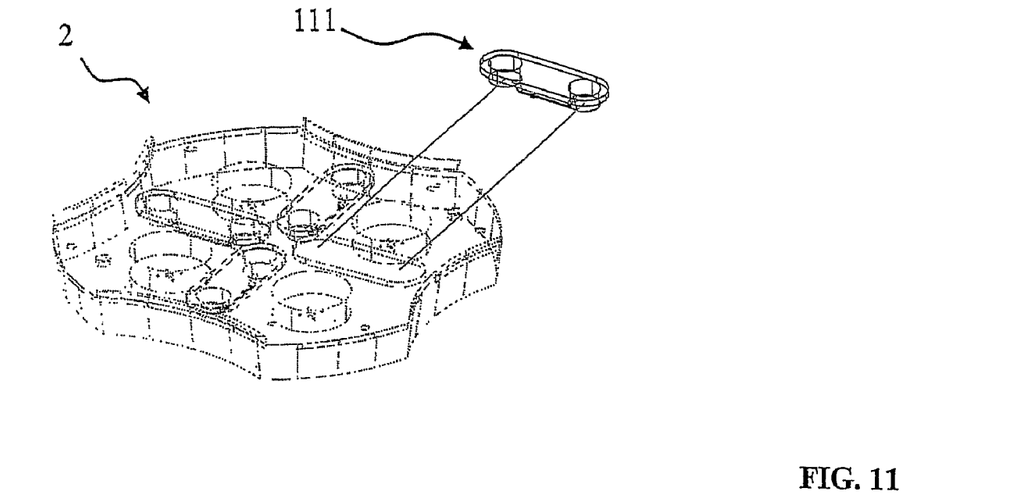
FIG. 11 shows the principle in system with exchangeable micro-channel units may be used.

In FIG. 11 is illustrated an embodiment of the invention showing the principle in an exchangeable system where different sizes of micro channel units 111 may be used. The unique functionality in the design makes it possible to change individual micro culture channel units 111 with other micro culture units having different dimensions or functions. This is another aspect which makes the culture dish 1 more versatile.

Figure 12:
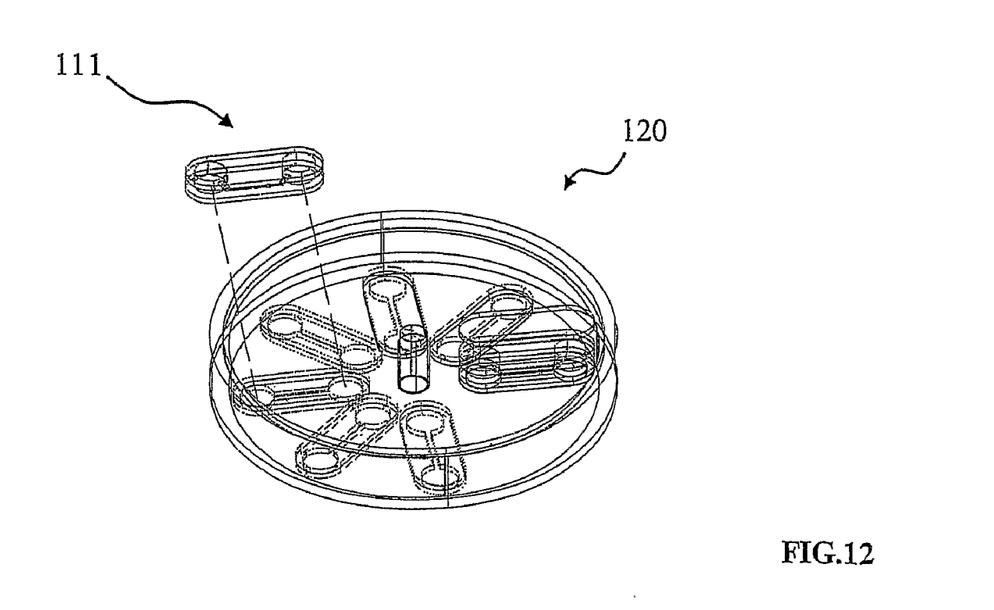
FIG. 12 shows a warming block for micro-channel units

In FIG. 12 is illustrated, where the individual micro culture channel units 111 may be placed in a warming block 120. The warming block 120 has the same kind of lid 3 as the culture dish 1. The warning block 120 may be round, rectangular or of any other desirable form and contain a plurality of microchannel units 111, macro wells 4 and micro-wells (60, 61) or a combination of them.

Figure 13:
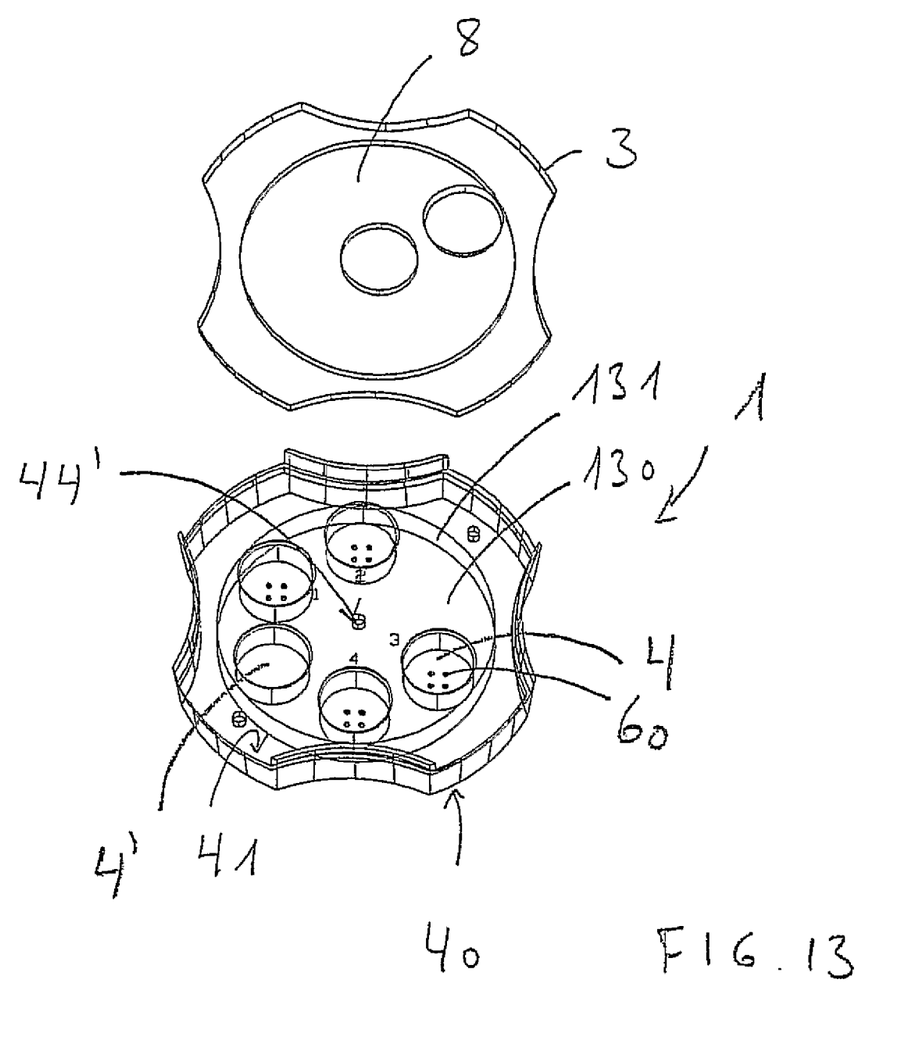
FIG. 13 is an alternative embodiment of the culture dish.

In FIG. 13, an alternative embodiment of a culture dish 1 according to the invention is shown. This dish 1 comprises five macro wells 4, of which four have micro wells 60 and are used for culturing and wherein the fifth well 4' without micro wells is used for cleaning/flushing purposes. This culture dish 1 further comprises a circular region 130 enclosed by a circular wall 131, inside which, the temperature buffering water reservoir is located. This circular wall 131 in the bottom cup 40 has the advantage, that it is easily and safely tightened against the corresponding sealing ring in the top part 41 when the culture dish 1 is assembled. Water can be filled into the reservoir inside the wall 131 through a central opening 44'. Alternatively, the dish could comprise of five macro wells with micro wells and five macro wells with no micro wells.

As described in the foregoing, the culture dish according to the invention provides a number of related solutions in order to improve the art of culture dishes for IVF.

The invention claimed is:

1. A culture dish (1) comprising a basic structure (2) with a number of macro wells (4) for culturing oocytes, the culture dish further comprising a lid (3) with a movable part (8), the movable part (8) having an opening (11) adapted to the size of the macro wells (4), the movable part (8) being movable between a first position where all macro wells are closed by the lid (3) and further positions where for each further position the opening (11) is aligned with one of the macro wells (4) to allow access to only one macro well (4) at a time through the opening (11) in the lid (3).

2. A culture dish according to claim 1, wherein the movable part is a rotational disc (8) that is rotatable between the first position and the further positions.

3. A culture dish according to claim 2, wherein the lid (3) is configured to have a low state in the first position in order to tightly cover the wells (4) in the first position and where the lid (3) has a lifted state at the further positions in order to prevent scraping of condensations during rotation.

4. A culture dish according to claim 1, wherein the movable part (8) is configured with elevations as scoops (17) adapted to the macro wells for gathering of condensation in the scoops in order to prevent scraping of condensation from the movable part (8) during movements of the movable part.

5. A culture dish according to claim 1, wherein the basic structure (2) comprises a bottom cup (40) and a top part (41) with a cavity between the bottom cup (40) and the top part (41), the top part (41) comprising the wells (4), the walls of the wells (4) extending into the cavity for thermal contact with a fluid in the cavity in order for the cavity to act as a heat reservoir for the wells when liquid is present in the cavity.

6. A culture dish according to claim 5, wherein the cavity extends around the side walls of the wells (4) and underneath the bottom of the wells (4).

7. A culture dish according to claim 1, further comprising at least one pair of handling wells (14), the two handling wells (14) of the at least one pair being connected by a micro channel (5), the diameter of the micro channel (5) having a size adapted to the size of an oocyte.

8. A culture dish according to claim 7, wherein the micro channel (5) comprises a resting chamber (64) with an obstacle (92) for preventing an oocyte (91) to pass the obstacle (92) but for allowing fluid to pass the obstacle.

9. A culture dish according to claim 7, wherein the at least one pair of handling wells (42, 62) and the micro channel (5) are constructed as a unit (111), the unit being placeable and exchangeable in the top part (41).

10. A culture dish according to claim 1, wherein the culture dish comprises a temperature indicator (50, 51) for indicating the temperature of the culture medium in the wells.

11. A culture dish according to claim 1, wherein the culture dish comprises an RFID tag for identification.

12. A culture dish according to claim 1, wherein the culture dish comprises at least one sensor for measuring temperature, pH or carbon dioxide concentration of the culture, wherein the sensor has an electronic readout.

13. A culture dish according to claim 12, wherein the culture dish comprises a micro processor connected to the electronic readout for receiving and processing electronic signals from the sensor.

14. A culture dish according to claim 13, wherein the micro processor is programmed to create an alarm signal when the at least one sensor measures parameters outside a predetermined range.

15. A culture dish according to claim 14, wherein the culture dish comprises an active RFID tag that is electronically coupled to the micro processor for transmission of data from the micro processor to a remote computer.

16. A combination of a culture dish according to claim 11 and an ID indicator intended to be worn by a person with which the culture dish is related, wherein the ID indicator and the RFID tag have means for mutual association.

* * * * *